(12) United States Patent
Miki et al.

(10) Patent No.: US 8,785,651 B2
(45) Date of Patent: Jul. 22, 2014

(54) METHOD FOR MANUFACTURING A BORONIC ACID ESTER COMPOUND

(75) Inventors: Takashi Miki, Toyonaka (JP); Yasuharu Shimasaki, Toyonaka (JP); Srinivasan Babu, South San Francisco, CA (US); Zhigang Cheng, South San Francisco, CA (US); Mark E. Reynolds, South San Francisco, CA (US); Qingping Tian, South San Francisco, CA (US)

(73) Assignees: Sumitomo Chemical Company, Limited, Tokyo (JP); Genentech, Inc., South San Francisco, CA (US)

( * ) Notice: Subject to any disclaimer, the term of this patent is extended or adjusted under 35 U.S.C. 154(b) by 291 days.

(21) Appl. No.: 13/142,536

(22) PCT Filed: Mar. 24, 2009

(86) PCT No.: PCT/US2009/038029
§ 371 (c)(1),
(2), (4) Date: Sep. 23, 2011

(87) PCT Pub. No.: WO2010/110782
PCT Pub. Date: Sep. 30, 2010

(65) Prior Publication Data
US 2012/0123122 A1    May 17, 2012

(51) Int. Cl.
*C07F 5/04* (2006.01)
*C07F 5/02* (2006.01)

(52) U.S. Cl.
USPC .............................. 548/110; 546/13

(58) Field of Classification Search
USPC ........................... 546/13; 548/110
See application file for complete search history.

(56) References Cited

U.S. PATENT DOCUMENTS

| 6,399,779 B1 | 6/2002 | Marcuccio et al. |
| 2002/0032339 A1 | 3/2002 | Marcuccio et al. |
| 2003/0032838 A1 | 2/2003 | Marcuccio et al. |
| 2006/0281925 A1 | 12/2006 | Itahashi et al. |

FOREIGN PATENT DOCUMENTS

| CN | 1255123 A | 5/2000 |
| JP | 2002-505663 A | 2/2002 |
| JP | 2003-512382 A | 4/2003 |
| WO | 98/45265 A1 | 10/1998 |
| WO | 01/29051 A1 | 4/2001 |
| WO | 2006/046031 A1 | 5/2006 |
| WO | 2006/046035 A1 | 5/2006 |
| WO | 2006/046040 A1 | 5/2006 |
| WO | 2007/127175 A2 | 11/2007 |
| WO | 2007/127183 A1 | 11/2007 |
| WO | 2007/129161 A2 | 11/2007 |
| WO | 2007/132171 A1 | 11/2007 |
| WO | 2008/070740 A1 | 6/2008 |
| WO | 2008/073785 A2 | 6/2008 |
| WO | 2009/055730 A1 | 4/2009 |

OTHER PUBLICATIONS

First Office Action issued Aug. 23, 2013 in counterpart Chinese Patent Application No. 200980158214.9 with English translation.
Notice of Reasons for Rejection issued Sep. 10, 2013 in counterpart Japanese Patent Application No. P2012-501971 with English translation.
Tatsuo Ishiyama, et al., "Palladium (0)-Catalyzed Cross-Coupling Reaction of Alkoxydiboron with Haloarenes: A Direct Procedure for Arylboronic Esters," Journal of Organic Chemistry, 1995, pp. 7508-7510, vol. 60, No. 23.
International Search Report of PCT/US2009/038029 dated Jan. 13, 2010.
C. Someswara Rao, "The Chemistry of Process Development," Fine Chemical & Pharmaceutical Industry, Second Edition, John Wiley & sons, LTD, p. 981, 2007.
The State Intellectual Property Office of the People's Republic of China, "The Second Office Action," issued in connection with Chinese Patent Application No. 200980158214.9, dated Apr. 9, 2014.

*Primary Examiner* — Charanjit Aulakh
(74) *Attorney, Agent, or Firm* — Sughrue Mion, PLLC

(57) ABSTRACT

The present invention relates to a method for manufacturing a boronic acid ester compound, characterized by reacting an aryl halide compound and a diboron ester compound in the presence of a nitrogen-containing organic base, a nickel catalyst, a phosphine compound and a solvent. According to the manufacturing method of the present invention, even if a nickel catalyst is used as the catalyst, a desired boronic acid ester compound can be obtained in a sufficiently high yield. Furthermore, even if aryl chloride or aryl bromide having relatively low price and low reactivity, was used as the aryl halide compound, a desired boronic acid ester compound can be obtained in a sufficiently high yield.

23 Claims, No Drawings

METHOD FOR MANUFACTURING A BORONIC ACID ESTER COMPOUND

CROSS REFERENCE TO RELATED APPLICATION

This application is a National Stage of International Application No. PCT/US2009/038029 filed Mar. 24, 2009, the contents of all of which are incorporated herein by reference in their entirety.

TECHNICAL FIELD

The invention relates to a method for manufacturing a boronic acid ester compound.

BACKGROUND ART

A boronic acid ester compound is a useful compound as e.g., an intermediate for synthesizing medical/agricultural drugs. The boronic acid ester compound has been manufactured generally by reacting an aryl halide and a diboron compound in the presence of a palladium catalyst (see, non-patent document 1, etc.).

However, use of a palladium catalyst has a problem. Generally, it is difficult to remove the catalyst from a product. In particular, in synthesizing medical/agricultural drugs, it is necessary to obtain a product with extremely high purity; however, if purification is repeatedly performed several times in order to increase the purity, the yield of the product significantly decreases (see, non-patent document 2, etc.).

In contrast, patent documents 1 and 2 exemplify a method for manufacturing a boronic acid ester compound using a nickel catalyst, which is easily removable by washing with water, etc. and relatively inexpensive.

However, conventional methods for manufacturing a boronic acid ester compound using a nickel catalyst described, for example, in patent documents 1 and 2 have a problem in insufficient yield.

[Patent document 1] WO 98/45265
[Patent document 2] U.S. 2003/0032838
[Non-patent document 1] Journal of Organic Chemistry 60 (23), 7508 (1995)
[Non-patent document 2] C. Someswara Rao, The Chemistry of Process Development in Fine Chemical & Pharmaceutical Industry Second Edition (John Wiley & sons, LTD, p. 981)

DISCLOSURE OF THE INVENTION

Problem to be Solved by the Invention

An object of the present invention to provide a method for manufacturing a boronic acid ester compound, capable of providing a desired product in a sufficiently high yield with a nickel catalyst.

Means for Solving the Problems

The present invention provides the following [1] to [24].

[1] A method for manufacturing a boronic acid ester compound represented by formula (3):

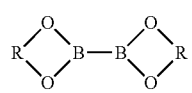

wherein Ar represents an optionally substituted aromatic hydrocarbon group or an optionally substituted aromatic heterocyclic group; and R represents a divalent organic group;

characterized by reacting a compound represented by formula (1):

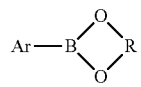

wherein Ar is as defined above, X represents a halogen atom, an optionally substituted alkylsulfonyloxy group, or an optionally substituted arylsulfonyloxy group;

with a compound (diboron compound) represented by formula (2):

wherein R is as defined above;

in the presence of a nitrogen-containing organic base, a nickel catalyst, a phosphine compound and a solvent.

[2] The method for manufacturing the boronic acid ester compound according to [1], in which Ar is an optionally substituted aromatic hydrocarbon group, an optionally substituted nitrogen-containing aromatic heterocyclic group, an optionally substituted sulfur-containing aromatic heterocyclic group, or an optionally substituted oxygen-containing aromatic heterocyclic group.

[3] The method for manufacturing the boronic acid ester compound according to [1], in which Ar is an optionally substituted aromatic hydrocarbon group, or an optionally substituted nitrogen-containing aromatic heterocyclic group.

[4] The method for manufacturing the boronic acid ester compound according to [1], in which Ar is an optionally substituted phenyl group, an optionally substituted pyridyl group, an optionally substituted indolyl group, or an optionally substituted indazolyl group.

[5] The method for manufacturing the boronic acid ester compound according to any one of [1] to [4], in which the nickel catalyst is a 0-valent or divalent nickel complex.

[6] The method for manufacturing the boronic acid ester compound according to any one of [1] to [4], in which the nickel catalyst is at least one nickel complex selected from the group consisting of a nickel(0)-alkene complex, a nickel(0)-phosphine complex, a nickel(0)-phosphite complex, an inorganic acid salt of nickel(II), an organic acid salt of nickel(II), a nickel(II) halide, and a nickel(II) halide-phosphine complex.

[7] The method for manufacturing the boronic acid ester compound according to any one of [1] to [4], in which the nickel catalyst is bis(1,5-cyclooctadiene)nickel(0), nickel(II) nitrate or nickel(II) chloride.

[8] The method for manufacturing the boronic acid ester compound according to any one of [1] to [7], in which the nitrogen-containing organic base is a tertiary amine compound or a cyclic amidine compound.

[9] The method for manufacturing the boronic acid ester compound according to any one of [1] to [7], in which the nitrogen-containing organic base is a trialkylamine compound, a cyclic tertiary amine compound or a cyclic amidine compound.

[10] The method for manufacturing the boronic acid ester compound according to any one of [1] to [7], in which the nitrogen-containing organic base is triethylamine, diisopropylethylamine, N-methylmorpholine or 1,8-diazabicyclo[5.4.0]-7-undecene.

[11] The method for manufacturing the boronic acid ester compound according to any one of [1] to [10], in which the phosphine compound is a triarylphosphine.

[12] The method for manufacturing the boronic acid ester compound according to any one of [1] to [10], in which the phosphine compound is triphenylphosphine.

[13] The method for manufacturing the boronic acid ester compound according to any one of [1] to [12], in which the solvent is an alcohol solvent, or a mixed solvent of an alcohol solvent and at least one solvent selected from the group consisting of a hydrocarbon solvent, an ether solvent, an ester solvent, a ketone solvent, an amide solvent, a nitrile solvent, a sulfoxide solvent and a halogenated hydrocarbon solvent.

[14] The method for manufacturing the boronic acid ester compound according to any one of [1] to [12], in which the solvent is an alcohol solvent, or a mixed solvent of an alcohol solvent and at least one solvent selected from the group consisting of a hydrocarbon solvent, an ether solvent, and an ester solvent.

[15] The method for manufacturing the boronic acid ester compound according to [13] or [14], in which the alcohol solvent is methanol or ethanol.

[16] The method for manufacturing the boronic acid ester compound according to [13] or [14], in which the alcohol solvent is methanol.

[17] The method for manufacturing the boronic acid ester compound according to any one of [1] to [16], in which R is an optionally substituted alkylene group, or an optionally substituted arylene group.

[18] The method for manufacturing the boronic acid ester compound according to any one of [1] to [17], in which the compound represented by formula (2) is bis(pinacolate)diboron.

[19] The method for manufacturing the boronic acid ester compound according to any one of [1] to [18], in which X is a chlorine atom, a bromine atom, an iodine atom, a methanesulfonyloxy group, a trifluoromethanesulfonyloxy group, a toluenesulfonyloxy group or a benzenesulfonyloxy group.

[20] The method for manufacturing the boronic acid ester compound according to any one of [1] to [18], in which X is a chlorine atom, a bromine atom, or an iodine atom.

[21] The method for manufacturing the boronic acid ester compound according to [1], in which Ar is an aromatic heterocyclic group selected from the group consisting of the following:

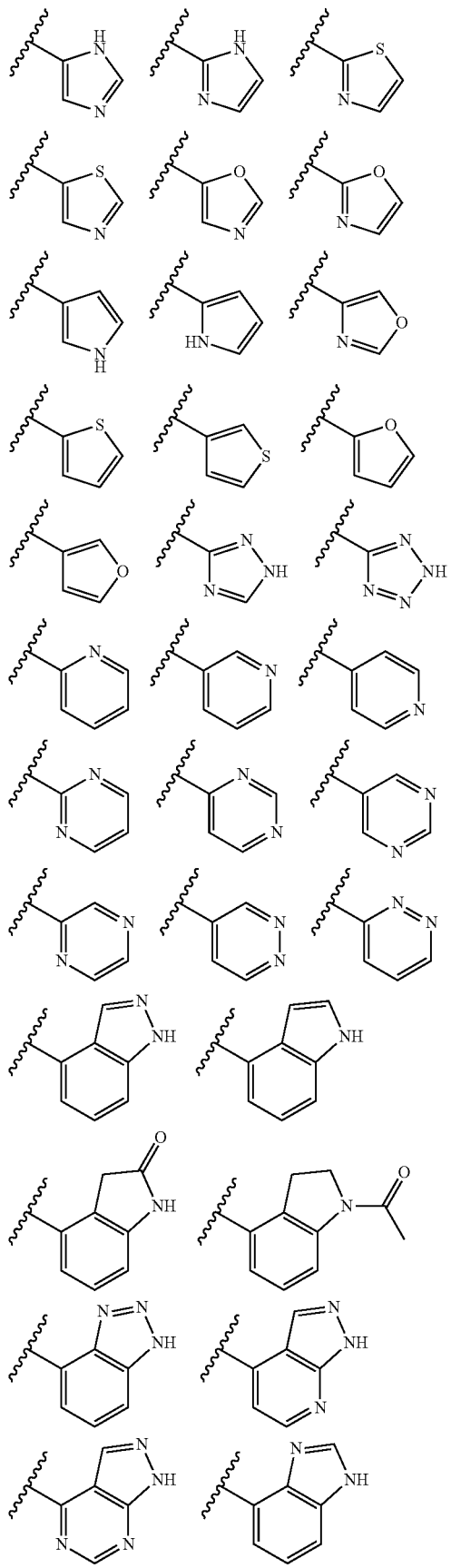

-continued

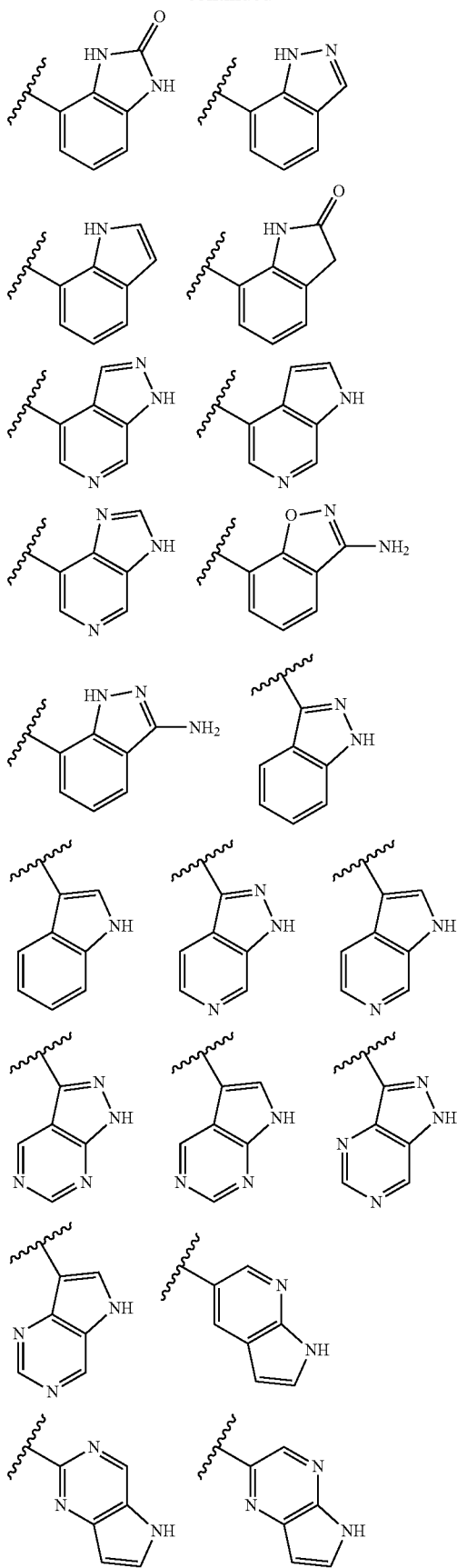
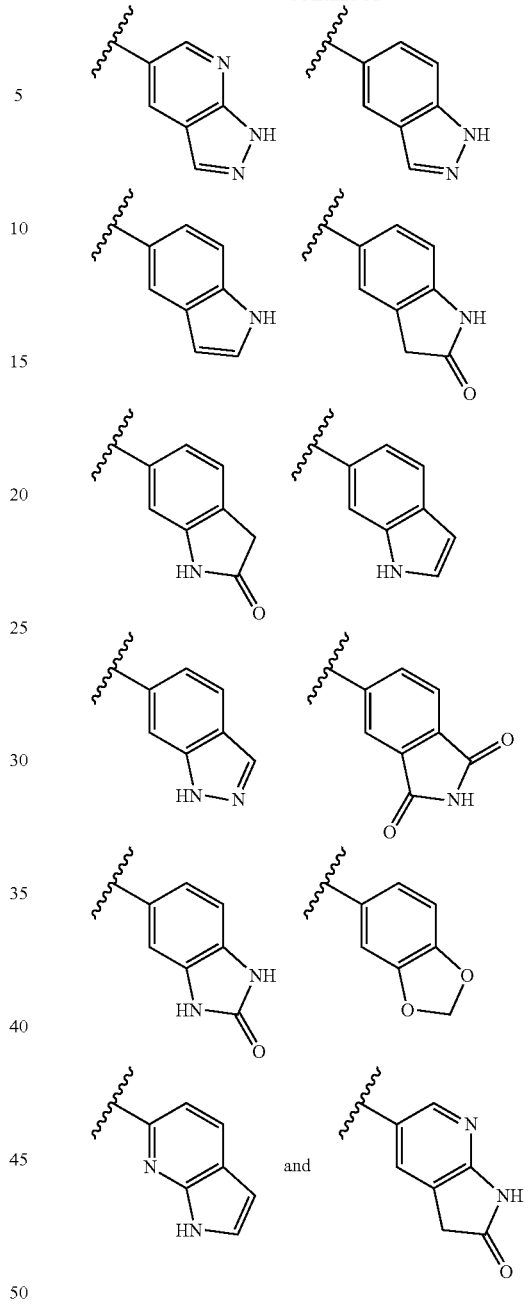

where the wavy lines indicate the bonding position of Ar, and the above groups may be substituted.

[22] The method for manufacturing the boronic acid ester compound according to [21], in which the aromatic heterocyclic group is substituted with one or more groups selected from the group consisting of a fluorine atom, a chlorine atom, a bromine atom, an iodine atom, a methyl group, a cyano group, a trifluoromethyl group, a hydroxymethyl group, a carboxy group, a carbamoyl group, an N,N-dimethylcarbamoyl group, a nitro group, an amino group, an N-methylamino group, N-acetylamino group, a hydroxy group, a methoxy group, a sulfanyl group, a methylsulfonyl group, and a group represented by the formula —NHC(=O)NHCH$_3$.

[23] The method for manufacturing the boronic acid ester compound according to [1], wherein the compound represented by formula (1) is the compound represented by the following formula:

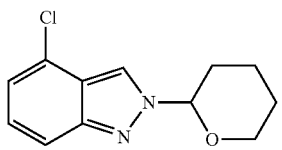 [SMILES: Clc1cccc2nn(C3CCCCO3)cc12]

[24] The method for manufacturing the boronic acid ester compound according to [1], wherein the compound represented by formula (3) is the compound represented by the following formula:

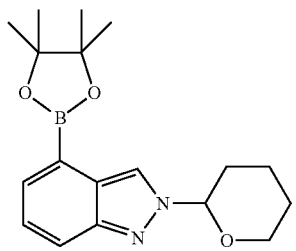 [SMILES: CC1(C)OB(c2cccc3nn(C4CCCCO4)cc23)OC1(C)C]

Advantages of the Invention

According to the method for manufacturing a boronic acid ester compound of the present invention, a desired product can be obtained in a sufficiently high yield even if a nickel catalyst is used as the catalyst.

Furthermore, in a conventional method for manufacturing the boronic acid ester compound using a nickel catalyst, it is necessary to use aryl iodide having a relatively high price and high reactivity, as an aryl halide serving as a raw material. However, according to the present invention, even if aryl chloride or aryl bromide having a relatively low price and low reactivity, is used, a desired product can be obtained in a sufficiently high yield.

Moreover, according to the method for manufacturing a boronic acid ester compound of the present invention, the reaction proceeds in mild conditions compared to a conventional method where a palladium catalyst or a nickel catalyst is used.

Exemplary embodiments of the present invention will be more specifically described below; however, the present invention is not limited to the following Examples.

[Compound Represented by Formula (1)]

In the "optionally substituted aromatic hydrocarbon group" of Ar above, the "aromatic hydrocarbon group" is preferably an aryl group of 6 to 20 carbon atoms. Specific examples thereof may include a phenyl group, a naphthyl group, a fluorenyl group, a phenanthryl group, and an anthryl group.

In the "optionally substituted aromatic heterocyclic group" of Ar above, the "aromatic heterocyclic group" is preferably a nitrogen-containing aromatic heterocyclic group, a sulfur-containing aromatic heterocyclic group or an oxygen-containing aromatic heterocyclic group, and more preferably a nitrogen-containing aromatic heterocyclic group.

As a specific example of the sulfur-containing aromatic heterocyclic group, a thienyl group may be mentioned. Note that the sulfur-containing aromatic heterocyclic group may be an aromatic heterocyclic group containing both sulfur and nitrogen such as a thiazolyl group or a benzothiazolyl group.

As a specific example of the oxygen-containing aromatic heterocyclic group, a furyl group and an isobenzofuranyl group may be mentioned. Note that the oxygen-containing aromatic heterocyclic group may be an aromatic heterocyclic group containing both oxygen and nitrogen such as an oxazolyl group or a benzoxazolyl group.

Specific examples of the nitrogen-containing aromatic heterocyclic group may include an indolyl group, an indazolyl group, a benzotriazolyl group, a quinolyl group, a phthalazinyl group, a quinoxalinyl group, a quinazolinyl group, a pyrrolyl group, an imidazolyl group, a pyrazolyl group, a pyridyl group, pyrimidinyl group, and a pyridazinyl group.

When the nitrogen-containing aromatic heterocyclic group has an NH residue, the NH residue may be protected with a protecting group including an optionally substituted aralkyloxycarbonyl group such as a benzyloxycarbonyl groups; an optionally substituted alkoxycarbonyl group such as a tert-butoxycarbonyl group; an optionally substituted allyloxycarbonyl group such as an allyloxycarbonyl group; an optionally substituted cyclic ether-2-yl group such as a tetrahydro-2H-pyran-2-yl group, a tetrahydrofuran-2-yl group, a 3-bromotetrahydrofuran-2-yl group, or a 1,4-dioxane-2-yl group; an optionally substituted aralkyl group such as a benzyl group; an optionally substituted sulfonyl group such as a p-toluenesulfonyl group; and an optionally substituted acyl group such as an acetyl group.

Note that the phrase "optionally substituted" in the explanation for the protecting group above means that a target group may have a substituent such as an aliphatic hydrocarbon group, an aromatic hydrocarbon group, a halogen atom, an optionally substituted acyl group, a hydroxy group, an alkoxy group, a cyano group, or a nitro group.

Furthermore, the phrase "optionally substituted" in the explanation for Ar above means that a target group may have a substituent such as an aliphatic hydrocarbon group, an aromatic hydrocarbon group, an aromatic heterocyclic group, or a characteristic group other than these.

Specific examples of the aliphatic hydrocarbon group may include a straight, branched or cyclic alkyl group of 1 to 20 carbon atoms such as a methyl group, an ethyl group, an isopropyl group, an isobutyl group, a tert-butyl group, a cyclohexyl group, an adamantyl group, or a dodecyl group; a straight, branched or cyclic alkenyl group of 2 to 20 carbon atoms such as a vinyl group, an allyl group, an isopropenyl group, a cyclohexenyl group, or an octadienyl group; and a straight, branched or cyclic alkynyl group of 2 to 20 carbon atoms such as an ethynyl group, a propynyl group, or a dodecynyl group. These groups may be further substituted with the aforementioned aromatic hydrocarbon groups or other characteristic groups later described. Also, not less than two aliphatic hydrocarbon groups may be joined to form a ring.

Specific examples of the aromatic hydrocarbon group may include the same groups as described above. Note that the aromatic hydrocarbon group may be further substituted with an aliphatic hydrocarbon group, an aromatic hydrocarbon group as mentioned above, and/or other characteristic groups later described.

Specific examples of the aromatic heterocyclic group may include the same groups as described above.

Specific examples of the aforementioned other characteristic groups may include a halogen atom such as a fluorine atom, a chlorine atom, a bromine atom, or an iodine atom; a carboxy group; an optionally substituted alkoxycarboxy group such as a methoxycarbonyl group; a formyl group; an acyl group such as an acetyl group; an optionally substituted alkoxy group such as a methoxy group, or a benzyloxy group; an optionally substituted carbamoyl group such as a carbamoyl group, or an N,N-dimethylcarbamoyl group; an amino group optionally protected with a protecting group as mentioned above such as an amino group, an N-methylamino group, an N-tert-butoxycarbonylamino group, or an N-acetylamino group; an imino group such as an imino group formed by dehydration-condensation of a formyl group or an acetyl group and an amino group; an optionally substituted sulfonyl group such as a benzenesulfonyl group; an optionally substituted alkylthio group such as a methylthio group; a thioxo group; a cyano group; a hydroxy group; a sulfanyl group; a nitro group; and a group represented by formula —NHC(=O)NHCH$_3$.

Note that the phrase "optionally substituted" in the explanation for other characteristic groups above means that a target group may have a substituent(s) such as an aliphatic hydrocarbon group, an aromatic hydrocarbon group, and/or an aromatic heterocyclic group.

The aforementioned Ar is preferably an aromatic hydrocarbon group or a nitrogen-containing aromatic heterocyclic group, and more preferably a phenyl group, a pyridyl group, an indolyl group or an indazolyl group.

As the "halogen atom" in the aforementioned X, a chlorine atom, a bromine atom and an iodine atom may be mentioned.

Specific examples of the "optionally substituted alkylsulfonyloxy group" in the aforementioned X may include a trifluoromethanesulfonyloxy group and a methanesulfonyloxy group.

Specific examples of the "optionally substituted arylsulfonyloxy group" in the aforementioned X may include a toluenesulfonyloxy group, and a benzenesulfonyloxy group.

Note that the phrase "optionally substituted" in the explanation for the aforementioned X means that a target group may have a substituent including an alkyl group of 1 to 4 carbon atoms such as a methyl group, an isopropyl group or a tert-butyl group; a halogen atom such as a fluorine atom, a chlorine atom, a bromine atom or an iodine atom; an optionally substituted alkoxy group such as a methoxy group; and a cyano group.

The aforementioned X is preferably a chlorine atom, a bromine atom, an iodine atom, a methanesulfonyloxy group, a trifluoromethanesulfonyloxy group, a toluenesulfonyloxy group, or a benzenesulfonyloxy group, and more preferably a chlorine atom, a bromine atom, or an iodine atom.

Specific examples of a compound represented by formula (1) having Ar and X as mentioned above may include chlorobenzene, 4-chlorotoluene, 4-chloroanisole, 4-chloroacetophenone, 4-chlorobenzonitrile, 4-chloropyridine, 4-chloroindole, 2-amino-6-chlorotoluene, 4-chlorostyrene, 1-chloro-4-ethynylbenzene, 1-chloro-4-phenylbenzene, 1-chloro-4-fluorobenzene, 4-chlorobenzoic acid, methyl 4-chlorobenzoate, 4-chlorobenzoic acid amide, 2-(N-tert-butoxycarbonyl amino)-6-chlorotoluene, N-(3-chloro-2-methylphenyl)acetamide, 4-chlorophenol, 1-chloronaphthalene, 1-chlorophenanthrene, 1-chloroanthracene, 4-chlorobenzotriazole, 4-chloroquinoline, 5-chlorophthalazine, 5-chloropyrimidine, 4-chlorobenzothiazoline, 4-chlorobenzoisothiazoline, 4-chlorobenzooxazoline, 4-chlorobenzoisooxazoline, 1-(tert-butoxycarbonyl)-4-chloro-1H-indazole, 2-(tert-butoxycarbonyl)-4-chloro-2H-indazole, 4-chloro-1-(tetrahydro-2H-pyran-2-yl)-1H-indazole, 4-chloro-2-(tetrahydro-2H-pyran-2-yl)-2H-indazole, 4-chloro-1-(tetrahydrofuran-2-yl)-1H-indazole, 4-chloro-2-(tetrahydrofuran-2-yl)-2H-indazole, 1-acetyl-4-chloro-1H-indazole, and 2-acetyl-4-chloro-2H-indazole.

Furthermore, position isomers of these compounds; these compounds whose chlorine atom (chloro group) is substituted with a bromine atom, an iodine atom, a methanesulfonyloxy group, a benzenesulfonyloxy group, a trifluoromethanesulfonyloxy group or a toluenesulfonyloxy group; and the aforementioned compounds having an NH residue protected with a protecting group may be mentioned as specific examples of a compound represented by formula (1).

[Compound Represented by Formula (2)]

As the "divalent organic group" in the R above, an optionally substituted alkylene group (particularly having 2 to 6 carbon atoms) and an optionally substituted arylene group (particularly having 6 to 10 carbon atoms) may be mentioned.

In the "optionally substituted alkylene group" above, specific examples of the "alkylene group" may include an ethylene group, a propylene group, a butylene group, and a pentylene group.

In the "optionally substituted arylene group", specific examples of the "arylene group" may include a phenylene group and a benzophenylene group.

The phrase "optionally substituted" in the explanation for R above means that a target group may have a substituent including a straight, branched or cyclic alkyl group of 1 to 4 carbon atoms such as a methyl group, an isopropyl group, or a tert-butyl group; an aryl group of 6 to 10 carbon atoms such as a phenyl group, or a naphthyl group; an alkoxycarbonyl group such as an ethoxycarbonyl group, or an isopropoxycarbonyl group; and an optionally substituted carbamoyl group such as an N,N-dimethylcarbamoyl group. Note that the alkyl group above may have an aromatic hydrocarbon group as mentioned above as a substituent, and the aryl group above may have an aliphatic hydrocarbon group or an aromatic hydrocarbon group as a substituent.

As a specific example of a compound represented by formula (2) as mentioned above having R, the following compounds may be mentioned;

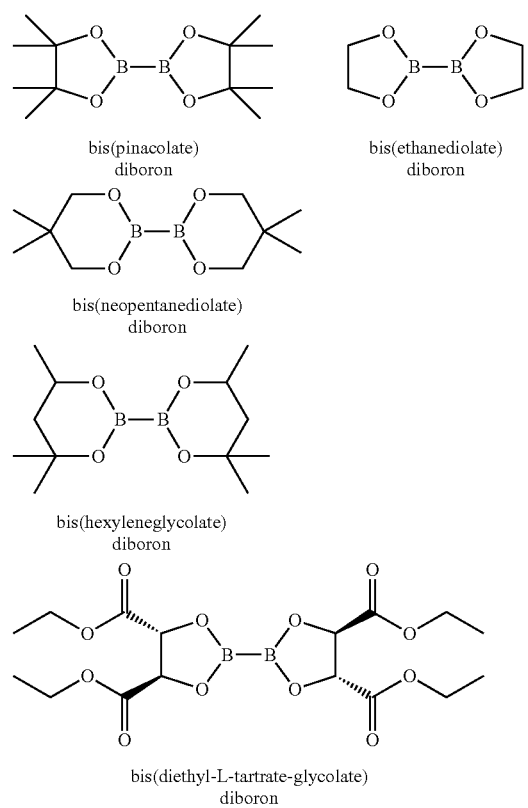

bis(pinacolate) diboron bis(ethanediolate) diboron bis(neopentanediolate) diboron bis(hexyleneglycolate) diboron bis(diethyl-L-tartrate-glycolate) diboron

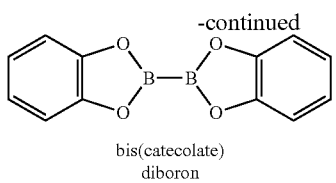

bis(catecolate)
diboron while bis(pinacolate)diboron, bis(ethanediolate)diboron, and bis(neopentanediolate)diboron are preferable and bis(pinacolate)diboron is more preferable.

The use amount of a compound represented by formula (2) as mentioned above is usually 1 to 30 fold by mole, preferably 1 to 5 fold by mole, and more preferably 1 to 2 fold by mole relative to the amount of a compound represented by formula (1) as mentioned above.

[Nitrogen-Containing Organic Base]

As the nitrogen-containing organic base, for example, an amine compound, a cyclic amidine compound, and an optionally substituted nitrogen-containing aromatic heterocyclic compound may be mentioned.

As the amine compound, for example, a primary amine compound (particularly having 1 to 10 carbon atoms), a secondary amine compound (particularly having 2 to 20 carbon atoms), and a tertiary amine compound (particularly having 3 to 40 carbon atoms) may be mentioned.

Specific examples of the primary amine compound may include methylamine, ethylamine, propylamine, isopropylamine, n-butyl amine, sec-butyl amine, tert-butyl amine, isobutylamine, and aniline.

Specific examples of the secondary amine compound may include dimethylamine, diethylamine, dipropylamine, diisopropylamine, dibutyl amine, N-methylaniline, and morpholine.

Specific examples of the tertiary amine compound may include optionally substituted trialkylamine compounds such as trimethylamine, triethylamine, tri-n-propylamine, tri-n-butylamine, tri-n-pentylamine, tri-n-hexylamine, tri-n-octylamine, tri-n-nonylamine, tri-n-decylamine, tri-n-undecylamine, tri-n-dodecylamine, diisopropylethylamine, and tribenzylamine; dialkylarylamine compounds such as N,N-dimethylaniline; and triarylamine compounds such as triphenylamine.

Cyclic tertiary amine compounds such as N-methylmorpholine, N-ethylmorpholine, N-methylpiperidine, and N-methylpyrrolidine may be mentioned.

Specific examples of the cyclic amidine compound may include 1,8-diazabicyclo[5.4.0]-7-undecene, and 1,5-diazabicyclo[4.3.0]-5-nonene.

Specific examples of the optionally substituted nitrogen-containing aromatic heterocyclic compound may include pyridine, N,N-dimethylaminopyridine, picoline, N-methylimidazole, and oxazole.

The nitrogen-containing organic base is preferably a tertiary amine compound or a cyclic amidine compound, more preferably a trialkylamine compound, a cyclic tertiary amine compound, or a cyclic amidine compound, and particularly preferably triethylamine, diisopropylethylamine, N-methylmorpholine, or 1,8-diazabicyclo[5.4.0]-7-undecene.

The use amount of the nitrogen-containing organic base is usually 1 to 30 fold by mole, preferably 1 to 10 fold by mole, and more preferably 1 to 5 fold by mole relative to the amount of a compound represented by formula (1) above.

[Nickel Catalyst]

As the nickel catalyst, for example, a nickel complex, a nickel alloy and a nickel-containing compound may be mentioned.

The nickel complex refers to a compound having a structure in which a nickel atom is arranged as the center and ligands are arranged around the nickel atom and bonded thereto. For example, a 0-valent nickel complex, and a divalent nickel complex may be mentioned.

Specific examples of the 0-valent nickel complex may include nickel(0) alkene complexes such as bis(1,5-cyclooctadiene)nickel(0); nickel(0)-phosphine complexes such as tetrakis (triphenylphosphine)nickel(0); and nickel(0)-phosphite complexes such as tetrakis(triphenylphosphite)nickel (0).

Specific examples of the divalent nickel complex may include inorganic acid salts of nickel(II) such as nickel(II) nitrate, nickel(II) sulfate, and nickel(II) carbonate; organic acid salts of nickel(II) such as nickel(II) trifluoromethanesulfonate, nickel(II) acetate, nickel(II) benzoate, and nickel (II) bis(acetylacetonate); nickel(II) halides such as nickel(II) fluoride, nickel(II) chloride, nickel(II) bromide, and nickel (II) iodide; nickel(II) halide-phosphine complexes such as bis(triphenylphosphine)nickel(II) chloride, and bis(triphenylphosphine)nickel(II) bromide; nickel(II) oxides; and nickel(II) hydroxides.

As the nickel alloy, for example, a nickel-metal in group 13 alloy may be mentioned. A nickel-aluminum alloy and Raney nickel are preferable.

As the nickel-containing compound, for example, a compound, where nickel is supported on an element in group 13 or 14, or a compound containing an element in group 13 or 14, may be mentioned, while nickel carbon and nickel alumina are preferable.

The nickel catalyst mentioned above is preferably a nickel complex; more preferably a nickel(0)-alkene complex, a nickel(0)-phosphine complex, a nickel(0)-phosphite complex, an inorganic salt of nickel(II), an organic acid salt of nickel(II), a nickel(II) halide, or a nickel(II) halide-phosphine complex; further preferably a nickel(0)-alkene complex, an inorganic salt of nickel(II), or a nickel(II) halide; and particularly preferably bis(1,5-cyclooctadiene)nickel(0), nickel(II) nitrate, or nickel(II) chloride.

These nickel catalysts may be commercially available ones and manufactured by any known method. Furthermore, the nickel catalysts may be hydrates or may be produced in a reaction system.

The use amount of the nickel catalyst above is usually 0.0001 to 0.5 fold by mole, preferably 0.001 to 0.3 fold by mole, and more preferably 0.01 to 0.1 fold by mole relative to the amount of a compound represented by formula (1) above.

[Phosphine Compound]

As the phosphine compound, phosphine compounds having an aromatic group such as a triarylphosphine, an alkyldiarylphosphine, and a bidentate phosphine compound having an aromatic group; and phosphine compounds having no aromatic group such as a trialkylphosphine, a bidentate phosphine compound having no aromatic group may be mentioned.

Specific examples of the triarylphosphine may include triphenylphosphine, tri(o-tolyl)phosphine, tri(m-tolyl)phosphine, tri(p-tolyl)phosphine, diphenyl(tolyl)phosphine, tris(dimethylphenyl)phosphine, trimesitylphosphine, tris(methoxyphenyl)phosphine, bis(methoxyphenyl)phenylphosphine, tris(fluorophenyl)phosphine, bis(pentafluorophenyl)phenylphosphine, trifurylphosphine, and trithienylphosphine. Specific examples of the alkyldiarylphosphine may include ethyldiphenylphosphine.

Specific examples of the bidentate phosphine compound having an aromatic group may include 1,2-bis(diphenylphosphino)ethane, 1,3-bis(diphenylphosphino)propane, bis(diphenylphosphino)ferrocene, 1-[2-(diphenylphosphino)ferrocenyl]ethyldicyclohexylphosphine, and 2,2'-bis(diphenylphosphino)-1,1'-binaphthyl.

Specific examples of the trialkylphosphine may include trifurylphosphine, tri(tert-butyl)phosphine, tri(n-hexyl)phosphine, tri(n-octyl)phosphine, tricyclopentylphosphine, and tricyclohexylphosphine.

Specific examples of the bidentate phosphine compound having no aromatic group may include 1,2-bis(diethylphosphino)ethane, 1,2-bis(dicyclohexylphosphino)ethane, and 1,3-bis (dicyclohexylphosphino)propane.

The phosphine compound above is preferably a phosphine compound having an aromatic group, more preferably a triarylphosphine, and particularly preferably triphenylphosphine.

These phosphine compounds may be commercially available ones and manufactured by any known method. Furthermore, when the nickel catalyst above has a phosphine as a ligand, a phosphine may not be necessarily added.

The use amount of the phosphine compound above is usually 0.0001 to 1.0 fold by mole, preferably 0.001 to 0.6 fold by mole, and more preferably 0.01 to 0.2 fold by mole relative to the amount of a compound represented by formula (1) above.

[Solvent]

As the solvent, for example, an alcohol solvent, a hydrocarbon solvent, an ether solvent, an ester solvent, a ketone solvent, an amide solvent, a nitrile solvent, a sulfoxide solvent, and a halogenated hydrocarbon solvent may be mentioned.

Specific examples of the alcohol solvent may include methanol, ethanol, 1-propanol, 2-propanol, 1-butanol, 2-methyl-1-propanol, 2-butanol, tert-butyl alcohol, pentanol, hexanol, ethylene glycol, glycerin, polyethylene glycol, 2-methoxyethanol, benzyl alcohol, and cyclohexanol.

Specific examples of the hydrocarbon solvent may include benzene, toluene, xylene, mesitylene, nitrobenzene, pentane, hexane, heptane, octane, cyclopentane, and cyclohexane.

Specific examples of the ether solvent may include tetrahydrofuran, 1,4-dioxane, diethyl ether, tert-butyl methyl ether, dimethoxyethane, cyclopentyl methyl ether, and diisopropyl ether.

Specific examples of the ester solvent may include methyl acetate, ethyl acetate, propyl acetate, isopropyl acetate, butyl acetate, methyl propionate, dimethyl carbonate, diethyl carbonate, and butyrolactone.

Specific examples of the ketone solvent may include acetone, methyl ethyl ketone, diethyl ketone, methyl isobutyl ketone, and acetophenone.

Specific examples of the amide solvent may include N,N-dimethylformamide, N,N-dimethylacetamide, N-methylpyrrolidone, and 1,3-dimethyl-2-imidazolidinone.

Specific examples of the nitrile solvent may include acetonitrile, propionitrile, butyronitrile, and benzonitrile.

Specific examples of the sulfoxide solvent may include dimethyl sulfoxide, diethyl sulfoxide, and sulfolane.

Specific examples of the halogenated hydrocarbon solvent may include dichloromethane, dichloroethane, chloroform, chlorobutane, fluoro benzene, and trifluoromethyl benzene.

The solvent is preferably an alcohol solvent or a mixed solvent of an alcohol solvent and at least one solvent selected from the group consisting of a hydrocarbon solvent, an ether solvent, an ester solvent, a ketone solvent, an amide solvent, a nitrile solvent, a sulfoxide solvent, and a halogenated hydrocarbon solvent; more preferably methanol or ethanol, or a mixed solvent of methanol or ethanol and at least one solvent selected from the group consisting of a hydrocarbon solvent, an ether solvent, an ester solvent, a ketone solvent, an amide solvent, a nitrile solvent, a sulfoxide solvent, and a halogenated hydrocarbon solvent; and particularly preferably methanol or a mixed solvent of methanol and at least one solvent selected from the group consisting of a hydrocarbon solvent, an ether solvent, and an ester solvent.

When the aforementioned mixed solvent is used, the ratio of the alcohol solvent is usually not less than 1% by mass, preferably not less than 10% by mass, and particularly preferably not less than 50% by mass relative to the total amount of the mixed solvent.

The use amount of the solvent above is usually not more than 500 fold by mass, preferably 0.1 to 100 fold by mass, and more preferably 1 to 30 fold by mass relative to the amount of a compound represented by formula (1) above.

[Preferable Combination of Nitrogen-Containing Organic Base, Nickel Catalyst and Phosphine Compound]

As a combination of a nitrogen-containing organic base, a nickel catalyst and a phosphine compound is preferably Nitrogen-containing organic base: tertiary amine compound or a cyclic amidine compound, Nickel catalyst: 0-valent or divalent nickel complex Phosphine compound: a phosphine compound having an aromatic group;

more preferably:

Nitrogen-containing organic base: a trialkylamine compound, a cyclic tertiary amine compound, or a cyclic amidine compound, Nickel catalyst: a Nickel(0)-alkene compound, or an inorganic salt of nickel(II) or nickel(II) halide, Phosphine compound: a triarylphosphine; and particularly preferably:

Nitrogen-containing organic base: triethylamine, diisopropylethylamine, N-methylmorpholine, or 1,8-diazabicyclo[5.4.0]-7-undecene;

Nickel catalyst: bis(1,5-cyclooctadiene)nickel(0), nickel nitrate (II), or nickel(II) chloride;

Phosphine compound: triphenylphosphine.

[Reaction Conditions and Others]

According to the manufacturing method of the present invention, a compound represented by formula (1) above is reacted with a compound represented by formula (2) above in the presence of a nitrogen-containing organic base, a nickel catalyst, a phosphine compound and a solvent as mentioned above to obtain a boronic acid ester compound represented by formula (3) above.

The reaction temperature of the aforementioned reaction is usually −40 to 150° C., preferably −20 to 100° C., and more preferably 0 to 80° C. The preferable reaction time varies depending upon the reaction conditions including reaction temperature and is usually one minute to 48 hours.

The order of mixing the aforementioned components is not particularly limited; however, any one of the following methods may be used:

after a compound represented by formula (2) above and a nitrogen-containing organic base are previously mixed in a solvent, a nickel catalyst, a phosphine compound and a compound represented by formula (1) above may be sequentially added;

after a compound represented by formula (2) above, a nitrogen-containing organic base, a nickel catalyst, and a phosphine compound are previously mixed in a solvent, a compound represented by formula (1) above may be added;

after a compound represented by formula (2) above, a nitrogen-containing organic base, and a compound represented by formula (1) above are previously mixed in a solvent, a nickel catalyst, and a phosphine compound may be added; and the aforementioned components are added simultaneously.

The proceeding of the reaction can be checked by general analysis means such as gas chromatography, high performance liquid chromatography, and/or NMR.

After completion of the reaction, the obtained reaction mixture is subjected to a general post treatment including a liquid separation treatment, a filtration treatment, a washing treatment, and a concentration treatment. In this manner, a boronic acid ester compound represented by formula (3) above can be isolated. As the aforementioned post treatment, more specifically, water is added to a reaction mixture to separate the liquid and the obtained organic phase is concentrated under reduced pressure, followed by washing with water. In addition to this method, a method in which a reaction mixture is concentrated under reduced pressure and thereafter washed with water, may be mentioned, for example.

An isolated boronic acid ester compound represented by formula (3) above may be further purified by a general purification treatment such as a silica gel column chromatographic treatment and a vaporization treatment. Furthermore, when a boronic acid ester compound represented by formula (3) above has crystallinity, a recrystallization treatment can be used for purification.

In the liquid separation treatment as mentioned above, when the solvent used in the reaction is capable of being dissolved both in water and an extraction solvent, it is desirable that the solvent is distilled off and thereafter the liquid separation treatment is performed. Furthermore, when a catalyst (no longer required) and insoluble impurities, etc. remain in the reaction mixture, it is desirable that these are removed by a filtration treatment and then a liquid separation treatment is performed.

As the extraction solvent to be used in the liquid separation treatment, for example, an ether solvent such as tert-butyl methyl ether, isopropyl ethyl ether or dimethoxyethane; an aromatic hydrocarbon solvent such as toluene; an aliphatic hydrocarbon solvent such as hexane, cyclohexane, or heptane; a halogenated hydrocarbon solvent such as dichloromethane, dichloroethane, chloroform, or chlorobenzene; an ester solvent such as ethyl acetate, methyl acetate, or butyl acetate; and a ketone solvent such as methylisobutyl ketone may be mentioned. When the same solvent as any one of these extraction solvents is used in the reaction, an operation of liquid separation can be directly performed.

To remove impurities such as a nickel catalyst remaining in a reaction mixture, washing may be performed with water, saline, acid, or a base. As the acid, for example, inorganic acids such as hydrogen chloride, hydrochloric acid, hydrobromic acid, sulfuric acid, and phosphoric acid; and organic acids such as acetic acid, citric acid, and methanesulfonic acid may be mentioned. As the base, inorganic bases such as ammonia, ammonia water, sodium hydroxide, sodium hydrogen carbonate, sodium carbonate, and potassium phosphate; and organic bases such as triethylamine, and pyridine may be mentioned. The use amounts of acid and base are not particularly limited; however, use may be made of within the range where a desired product is not affected.

As the solvent to be used for the recrystallization treatment mentioned above, for example, an aliphatic hydrocarbon solvent such as pentane, hexane or heptane; an aromatic hydrocarbon solvent such as benzene, toluene, or xylene; an alcohol solvent such as methanol, ethanol, propanol, isopropanol, or n-butanol; an ether solvent such as diethyl ether, tetrahydrofuran, or dimethoxyethane; a halogenated hydrocarbon solvent such as chloroform, dichloromethane, or dichloroethane; an amide solvent such as dimethylformamide, or dimethyl acetamide; a nitrile solvent such as acetonitrile; an ester solvent such as ethyl acetate; or water may be mentioned. These solvents may be used alone or not less than two types of solvents may be used simultaneously. Preferably, an aliphatic hydrocarbon solvent, an aromatic hydrocarbon solvent or a mixed solvent of these is used. The use amount of the solvent to be used for recrystallization is not particularly limited; usually falls within the range of 0.1 to 100 fold relative to the weight of the product obtained.

Specific examples of a boronic acid ester compound represented by formula (3) and obtained by the aforementioned manufacturing method of the present invention may include (4,4,5,5-tetramethyl-1,3,2-dioxaborolan-2-yl)benzene, 4-(4,4,5,5-tetramethyl-1,3,2-dioxaborolan-2-yl)toluene, 4-(4,4,5,5-tetramethyl-1,3,2-dioxaborolan-2-yl)anisole, 4-(4,4,5,5-tetramethyl-1,3,2-dioxaborolan-2-yl)acetophenone, 4-(4,4,5,5-tetramethyl-1,3,2-dioxaborolan-2-yl)benzonitrile, 4-(4,4,5,5-tetramethyl-1,3,2-dioxaborolan-2-yl)pyridine, 4-(4,4,5,5-tetramethyl-1,3,2-dioxaborolan-2-yl)indole, 2-amino-6-(4,4,5,5-tetramethyl-1,3,2-dioxaborolan-2-yl)toluene, 4-(4,4,5,5-tetramethyl-1,3,2-dioxaborolan-2-yl)styrene, 1-(4,4,5,5-tetramethyl-1,3,2-dioxaborolan-2-yl)-4-ethynylbenzene, 1-(4,4,5,5-tetramethyl-1,3,2-dioxaborolan-2-yl)-4-phenylbenzene, 1-(4,4,5,5-tetramethyl-1,3,2-dioxaborolan-2-yl)-4-fluorobenzene, 4-(4,4,5,5-tetramethyl-1,3,2-dioxaborolan-2-yl)benzoic acid, Methyl 4-(4,4,5,5-tetramethyl-1,3,2-dioxaborolan-2-yl)benzoate, 4-(4,4,5,5-tetramethyl-1,3,2-dioxaborolan-2-yl)benzoic acid amide, 2-(N-tert-butoxycarbonylamino)-6-(4,4,5,5-tetramethyl-1,3,2-dioxaborolan-2-yl)toluene, N-[3-(4',4',5',5'-tetramethyl-1',3',2'-dioxaborolan-2'-yl)-2-methylphenyl]acetamide, 4-(4,4,5,5-tetramethyl-1,3,2-dioxaborolan-2-yl)phenol, 1-(tert-butoxycarbonyl)-4-(4,4,5,5-tetramethyl-1,3,2-dioxaborolan-2-yl)-1H-indazole, 2-(tert-butoxycarbonyl)-4-(4,4,5,5-tetramethyl-1,3,2-dioxaborolan-2-yl)-2H-indazole, 4-(4,4,5,5-tetramethyl-1,3,2-dioxaborolan-2-yl)-1-(tetrahydro-2H-pyran-2-yl)-1H-indazole, 4-(4,4,5,5-tetramethyl-1,3,2-dioxaborolan-2-yl)-2-(tetrahydro-2H-pyran-2-yl)-2H-indazole, 4-(4,4,5,5-tetramethyl-1,3,2-dioxaborolan-2-yl)-1-(tetrahydrofuran-2-yl)-1H-indazole, 4-(4,4,5,5-tetramethyl-1,3,2-dioxaborolan-2-yl)-2-(tetrahydrofuran-2-yl)-2H-indazole, 1-acetyl-4-(4,4,5,5-tetramethyl-1,3,2-dioxaborolan-2-yl)-1H-indazole, 2-acetyl-4-(4,4,5,5-tetramethyl-1,3,2-dioxaborolan-2-yl)-2H-indazole, 1-(4,4,5,5-tetramethyl-1,3,2-dioxaborolan-2-yl)naphthalene, 1-(4,4,5,5-tetramethyl-1,3,2-dioxaborolan-2-yl)phenanthrene, 1-(4,4,5,5-tetramethyl-1,3,2-dioxaborolan-2-yl)anthracene, 4-(4,4,5,5-tetramethyl-1,3,2-dioxaborolan-2-yl)benzotriazole, 4-(4,4,5,5-tetramethyl-1,3,2-dioxaborolan-2-yl)quinoline, 5-(4,4,5,5-tetramethyl-1,3,2-dioxaborolan-2-yl)phthalazine, 5-(4,4,5,5-tetramethyl-1,3,2-dioxaborolan-2-yl)pyrimidine, 4-(4,4,5,5-tetramethyl-1,3,2-dioxaborolan-2-yl)benzothiazoline, 4-(4,4,5,5-tetramethyl-1,3,2-dioxaborolan-2-yl)benzoisothiazoline, 4-(4,4,5,5-tetramethyl-1,3,2-dioxaborolan-2-yl)benzooxazoline, and 4-(4,4,5,5-tetramethyl-1,3,2-dioxaborolan-2-yl)benzoisoxazoline.

Furthermore, the position isomers of these compounds may be also mentioned as specific examples of a boronic acid ester compound represented by formula (3).

EXAMPLES

The present invention will be more specifically described by way of Examples below; however, the present invention is not limited to the following Examples. Note that, in each example, 4-chloro-1-(tetrahydro-2H-pyran-2-yl)-1H-indazole is simply referred to as "chloro-THP-1H-indazole"; 4-chloro-2-(tetrahydro-2H-pyran-2-yl)-2H-indazole, as "chloro-THP-2H-indazole"; 1-(tetrahydro-2H-pyran-2-yl)-4-(4,4,5,5-tetramethyl-1,3,2-dioxaborolan-2-yl)-1H-indazole, as "THP-1H-indazole boronic acid pinacol ester"; and, 2-(tetrahydro-2H-pyran-2-yl)-4-(4,4,5,5-tetramethyl-1,3,2-dioxaborolan-2-yl)-2H-indazole as "THP-2H-indazole boronic acid pinacol ester".

Mixture of chloro-THP-1H-indazole and chloro-THP-2H-indazole

Manufacturing Example 1

Under a nitrogen atmosphere, a flask was charged with 4-chloroindazole (33.0 g (content: 91.0 wt %, 196.6 mmol)), pyridinium p-toluenesulfonate (0.49 g, (2.0 mmol)), 3,4-dihydro-2H-pyran (36.4 g, (432.6 mmol)), and dichloromethane (265 g). The obtained mixture was stirred at an interior temperature of 45° C. for 8 hours. The resultant reaction mixture was cooled to 25° C. To this, dichloromethane and water were added, stirred and then separated. To the obtained organic phase, a 5 wt % aqueous sodium hydrogen carbonate solution was added to wash. Thereafter, the organic phase was dried over anhydrous magnesium sulfate, concentrated under reduced pressure, and purified by silica gel column chromatography (mobile phase: hexane/ethyl acetate) to obtain an oily substance (48.5 g). The oily substance was analyzed by high performance liquid chromatography. As a result, the total content of chloro-THP-1H-indazole and chloro-THP-2H-indazole was 98.4 wt % (chloro-THP-1H-indazole:chloro-THP-2H-indazole=1:3.3, yield: 100%).

Manufacturing Example 2

Under a nitrogen atmosphere, a flask was charged with 4-chloroindazole (31.8 g (content: 94.3 wt %, 196.6 mmol)), pyridinium p-toluenesulfonate (0.99 g, (3.9 mmol)), 3,4-dihydro-2H-pyran (36.4 g, (432.6 mmol)), toluene (132 g) and heptane (132 g). The obtained mixture was heated to 40° C. and stirred for 9 hours. To the resultant reaction mixture, a 5% aqueous sodium hydrogen carbonate solution (101 g) was added. The mixture was cooled while mixing to 25° C., and then separated. To the obtained organic phase, a 5 wt % aqueous sodium hydrogen carbonate solution (101 g) was added again. After mixing/liquid separation was repeated twice, toluene (20 g) and sodium hydrogen carbonate (0.33 g) were added and concentrated under reduced pressure. To the concentrate, methanol was added and again subjected to concentration under reduced pressure and filtrated to obtain a filtrate (70.8 g). The filtrate was analyzed by high performance liquid chromatography. As a result, the total content of chloro-THP-1H-indazole and chloro-THP-2H-indazole was 65.2 wt % (chloro-THP-1H-indazole:chloro-THP-2H-indazole=1:13.7, yield: 100%).

Mixture of THP-1H-indazole boronic acid pinacol ester and THP-2H-indazole boronic acid pinacol ester

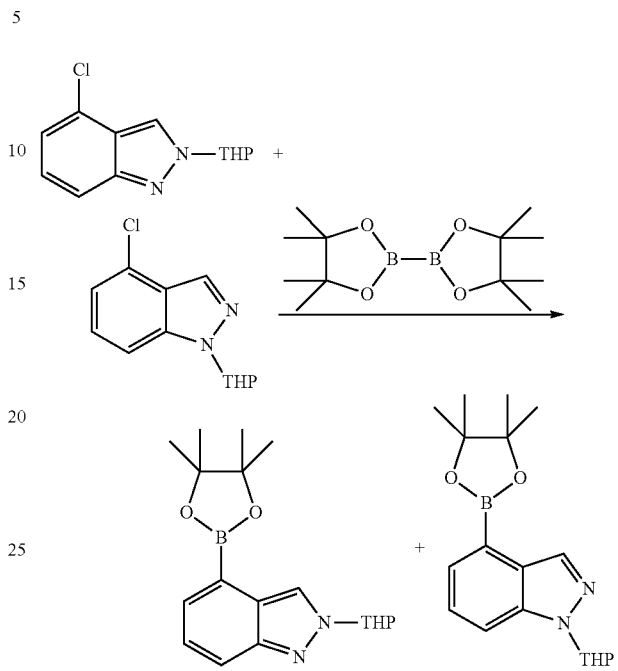

Example 1

Under a nitrogen atmosphere, a flask was charged with bis(pinacolate)diboron (55.8 g (0.22 mol)), methanol (120 g), triethylamine (44.5 g (0.44 mol)), and the mixture (61.3 g (total content: 65.2 wt %, 0.17 mol)) of chloro-THP-1H-indazole and chloro-THP-2H-indazole obtained in Manufacturing Example 2. While bubbling with nitrogen, the interior temperature was reduced to 0° C. Then, the flask was charged with nickel nitrate hexahydrate (2.0 g (6.8 mmol)) and triphenylphosphine (3.6 g (13.5 mmol)). The resultant reaction mixture was increased to an interior temperature of 5° C. and stirred for 22 hours. Thereafter, while the temperature was increased stepwise up to 15° C. for 6 hours, the mixture was stirred. The reaction mixture was analyzed by high performance liquid chromatography. As a result, the reaction mixture contained THP-1H-indazole boronic acid pinacol ester and THP-2H-indazole boronic acid pinacol ester in a total amount of 45.0 g (0.14 mol, reaction yield: 81%).

To the reaction mixture, tert-butyl methyl ether (440 g) and 5 wt % hydrochloric acid (168 g) were added. After the pH of the reaction mixture was adjusted to 7.5, liquid separation was performed. To the obtained water phase, tert-butyl methyl ether (360 g) was added to perform re-extraction. The organic phases individually obtained were combined, water phase was separated and the organic phase was concentrated under reduced pressure. To the resultant concentrate, toluene (160 g) was added and concentrated under reduced pressure. To the concentrate, toluene (120 g) and a 20 wt % aqueous methanol solution (150 g) were added, mixed and separated. Furthermore, to the resultant organic phase, a 20 wt % aqueous methanol solution (150 g) was added, mixed and separated. This operation was repeated twice. To the resultant organic phase, activated carbon (2.0 g) was added, stirred at room temperature for one hour and filtrated. The filtrate was concentrated under reduced pressure to obtain a concentrate (81.67 g). The obtained concentrate was analyzed by high performance liquid chromatography and gas chromatography. As a result, the concentrate contained THP-1H-indazole boronic acid pinacol ester and THP-2H-indazole boronic acid pinacol ester in an amount of 55.0 wt % (THP-1H-indazole boronic acid pinacol ester=3.0 wt %, THP-2H-indazole boronic acid pinacol ester=52.0 wt %, toluene=22.4 wt %). To the concentrate, toluene (8.55 g) and heptane (62.45 g) were added and heated to 45° C. To the mixture, a seed crystal (40 mg) containing a mixture of THP-1H-indazole boronic acid pinacol ester and THP-2H-indazole boronic acid pinacol ester was added. As a result, crystals precipitated. Thereafter, the mixture was cooled to 25° C. for 4 hours, again heated to 45° C., then cooled to 0° C. and filtrated. The crystals obtained was washed with a mixed solution (0° C.) of heptane (11.2 g) and toluene (4.8 g), filtrated, further washed with heptane (21.6 g) of 0° C. and filtrated. The remaining crystals were dried under reduced pressure to obtain crystals (33.9 g). The obtained crystals were analyzed by the high performance liquid chromatography internal standard method. As a result, the crystals contained no THP-1H-indazole boronic acid pinacol ester and contained only THP-2H-indazole boronic acid pinacol ester (30.03 g (91.5 mmol, content: 88.5 wt %, yield: 54%)). Furthermore, the mixture of the filtrates and washing solutions contained THP-1H-indazole boronic acid pinacol ester (10.4 g) and THP-2H-indazole boronic acid pinacol ester (2.3 g).

Example 2

Under a nitrogen atmosphere, a reaction vessel of 20 ml in volume was charged with bis(pinacolate)diboron (0.32 g (1.27 mmol)), degassed ethanol (3.6 ml), and triethylamine (0.26 g (2.53 mmol)). While the resultant mixture was stirred at an interior temperature of 25° C., bis(1,5-cyclooctadiene)nickel (9.3 mg (0.03 mmol)), triphenylphosphine (17.7 mg (0.07 mmol)), and a mixture (0.20 g (total content: 100.0 wt %, 0.85 mmol)) of chloro-THP-1H-indazole and chloro-THP-2H-indazole obtained in accordance with Manufacturing Example 1 were added to the mixture. After the resultant mixture was stirred at 30° C. for 5 hours, it was further stirred at 70° C. for one hour. The reaction mixture was analyzed by high performance liquid chromatography. As a result, the reaction mixture contained THP-1H-indazole boronic acid pinacol ester and THP-2H-indazole boronic acid pinacol ester in a total amount of 0.16 g (0.48 mmol, yield: 56%).

Example 3

Under a nitrogen atmosphere, a reaction vessel of 20 ml in volume was charged with bis(pinacolate)diboron (0.32 g (1.27 mmol)), degassed tert-butyl methyl ether (2.6 g), degassed methanol (0.3 g) and triethylamine (0.26 g (2.53 mmol)). While the resultant mixture was stirred at an interior temperature of 25° C., bis(1,5-cyclooctadiene)nickel (9.3 mg (0.03 mmol)), triphenylphosphine (17.7 mg (0.07 mmol)), and a mixture (0.20 g, (total content: 98.5 wt %, 0.85 mmol)) of chloro-THP-1H-indazole and chloro-THP-2H-indazole obtained in accordance with Manufacturing Example 1 were added to the mixture. After the resultant mixture was stirred at 30° C. for 3 hours, it was further stirred at 60° C. for one hour. The reaction mixture was analyzed by high performance liquid chromatography. As a result, the reaction mixture contained THP-1H-indazole boronic acid pinacol ester and THP-2H-indazole boronic acid pinacol ester in a total amount of 0.16 g (0.49 mmol, yield: 58%).

Examples 4 to 6

A reaction was performed in the same manner as in Example 3 except that the solvents listed in Table 1 were used in place of tert-butyl methyl ether, and the reaction temperature and reaction time were changed to those listed in Table 1. The results are shown in Table 1.

TABLE 1

|  | Example 4 | Example 5 | Example 6 |
|---|---|---|---|
| Solvent | Toluene | Ethyl acetate | Heptane |
| Reaction temperature/time | 1) 30° C./3 hours 2) 60° C./1 hour | 1) 30° C./3 hours 2) 60° C./1 hour | 30° C./3 hours |
| Yield | 68% | 46% | 69% |

Example 7

Under a nitrogen atmosphere, a reaction vessel of 20 ml in volume was charged with bis(pinacolate)diboron (0.64 g (2.53 mmol)), degassed methanol (7.2 g) and diisopropylethylamine (0.66 g (5.07 mmol)). While the resultant mixture was stirred at an interior temperature of 25° C., bis(1,5-cyclooctadiene)nickel (18.6 mg (0.07 mmol)), triphenylphosphine (35.5 mg (0.14 mmol)), and a mixture (0.45 g, (total content: 89.5 wt %, 1.69 mmol)) of chloro-THP-1H-indazole and chloro-THP-2H-indazole were added to the mixture. The resultant mixture was stirred at 30° C. for 5 hours. The reaction mixture was analyzed by high performance liquid chromatography. As a result, the reaction mixture contained THP-1H-indazole boronic acid pinacol ester and THP-2H-indazole boronic acid pinacol ester in a total amount of 0.39 g (1.19 mmol, yield: 70%).

Example 8

Under a nitrogen atmosphere, a reaction vessel of 20 ml in volume was charged with bis(pinacolate)diboron (0.64 g (2.53 mmol)), degassed methanol (3.0 g) and triethylamine (0.51 g (5.07 mmol)). While the resultant mixture was stirred at an interior temperature of 25° C., nickel nitrate hexahydrate (19.7 mg (0.07 mmol)), triphenylphosphine (35.5 mg (0.14 mmol)), and a mixture (0.45 g, (total content: 89.5 wt %, 1.69 mmol)) of chloro-THP-1H-indazole and chloro-THP-2H-indazole were added to the mixture. The resultant mixture was stirred at 30° C. for 6 hours. The reaction mixture was analyzed by high performance liquid chromatography. As a result, THP-1H-indazole boronic acid pinacol ester and THP-2H-indazole boronic acid pinacol ester were contained in a total amount of 0.45 g (1.37 mmol, yield: 81%).

Examples 9 and 10

A reaction was performed in the same manner as in Example 8 except that the use amounts of bis(pinacolate)diboron and triethylamine were individually changed to those listed in Table 2. The results are shown in Table 2.

TABLE 2

|  | Example 9 | Example 10 |
|---|---|---|
| Amount of bis(pinacolate)diboron | 0.56 g | 0.45 g |
| Amount of triethylamine | 0.45 g | 0.3 g |
| Yield | 80% | 61% |

Example 11

Under a nitrogen atmosphere, a reaction vessel of 20 ml in volume was charged with bis(pinacolate)diboron (0.24 g (0.95 mmol)), degassed methanol (2.9 g) and triethylamine (0.17 g (1.68 mmol)). While the resultant mixture was stirred at an interior temperature of 25° C., bis(1,5-cyclooctadiene) nickel (10 mg (0.04 mmol)), triphenylphosphine (18 mg (0.07 mmol)), and a mixture (0.20 g, (total content: 100 wt %, 0.84 mmol)) of chloro-THP-1H-indazole and chloro-THP-2H-indazole were added to the mixture. The resultant mixture was stirred at 30° C. for 3 hours. The reaction mixture was analyzed by high performance liquid chromatography. As a result, the reaction mixture contained THP-1H-indazole boronic acid pinacol ester and THP-2H-indazole boronic acid pinacol ester in a total amount of 0.19 g (0.57 mmol, yield: 68%).

Comparative Example 1

Under a nitrogen atmosphere, a reaction vessel of 20 ml in volume was charged with bis(pinacolate)diboron (0.12 g (0.47 mmol)), degassed methanol (1.4 g) and lithium methoxide (31 mg (0.82 mmol)). While the resultant mixture was stirred at an interior temperature of 25° C., bis(1,5-cyclooctadiene)nickel (3.0 mg (0.01 mmol)), triphenylphosphine (4.5 mg (0.02 mmol)), and a mixture (0.10 g, (total content: 97.7 wt %, 0.41 mmol)) of chloro-THP-1H-indazole and chloro-THP-2H-indazole were added to the mixture. The resultant mixture was stirred at 30° C. for 3.5 hours. Thereafter, bis(1,5-cyclooctadiene)nickel (3.0 mg (0.01 mmol)) and triphenylphosphine (4.5 mg (0.02 mmol)) were added and resultant mixture was again stirred at 30° C. for 2 hours. The reaction mixture was analyzed by high performance liquid chromatography. As a result, the reaction mixture contained THP-1H-indazole boronic acid pinacol ester and THP-2H-indazole boronic acid pinacol ester in a total amount of 22.9 mg (0.07 mmol, yield: 17%).

Comparative Examples 2 to 4

A reaction was performed in the same manner as in Comparative Example 1 except that the bases listed in Table 3 were used in place of lithium methoxide and the use amounts thereof were changed to those listed in Table 3. The results are shown in Table 3.

TABLE 3

| | Comparative Example 2 | Comparative Example 3 | Comparative Example 4 |
|---|---|---|---|
| Base | Sodium acetate | Cesium carbonate | Potassium phosphate |
| Charge amount | 83 mg | 275 mg | 180 mg |
| Yield | 0% | 0% | 3% |

Comparative Example 5

Under a nitrogen atmosphere, a reaction vessel of 20 ml in volume was charged with bis(pinacolate)diboron (0.32 g (1.26 mmol)), degassed dimethyl sulfoxide (3.6 g) and potassium acetate (0.25 g (2.54 mmol)). While the resultant mixture was stirred at an interior temperature of 25° C., bis(1,5-cyclooctadiene)nickel (10 mg (0.04 mmol)), triphenylphosphine (18 mg (0.07 mmol)), and a mixture (0.20 g, (total content: 100 wt %, 0.84 mmol)) of chloro-THP-1H-indazole and chloro-THP-2H-indazole were added to the mixture. The resultant mixture was stirred at 30° C. for 5 hours. Thereafter, the resultant mixture was further heated to 70° C. and stirred for 1 hour. The reaction mixture was analyzed by high performance liquid chromatography. As a result, neither THP-1H-indazole boronic acid pinacol ester nor THP-2H-indazole boronic acid pinacol ester were obtained in the reaction mixture (Yield: 0%).

Example 12

Under a nitrogen atmosphere, a reaction vessel of 20 ml in volume was charged with bis(pinacolate)diboron (0.64 g (2.5 mmol)), degassed methanol (7.2 g) and diisopropylethylamine (0.66 g (5.1 mmol)). While the resultant mixture was stirred at an interior temperature of 25° C., nickel nitrate hexahydrate (19.7 mg (0.07 mmol)), triphenylphosphine (35.5 mg (0.14 mmol)), and a mixture (0.45 g, (total content: 89.5 wt %, 1.69 mmol)) of chloro-THP-1H-indazole and chloro-THP-2H-indazole were added to the mixture. The resultant mixture was stirred at 30° C. for 5 hours. The reaction mixture was analyzed by high performance liquid chromatography. As a result, the reaction mixture contained THP-1H-indazole boronic acid pinacol ester and THP-2H-indazole boronic acid pinacol ester in a total amount of 0.36 g (1.2 mmol, yield: 70%).

Example 13

Under a nitrogen atmosphere, a reaction vessel of 20 ml in volume was charged with bis(pinacolate)diboron (0.32 g (1.27 mmol)), degassed methanol (2.8 g) and triethylamine (0.26 g (2.53 mmol)). While the resultant mixture was stirred at an interior temperature of 25° C., bis(1,5-cyclooctadiene) nickel (9.3 mg (0.03 mmol)), triphenylphosphine (17.7 mg (0.07 mmol)), and a mixture (0.20 g, (total content: 100.0 wt %, 0.85 mmol)) of chloro-THP-1H-indazole and chloro-THP-2H-indazole were added to the mixture. The resultant mixture was stirred at 30° C. for 3 hours. Thereafter, the resultant mixture was heated to 70° C. and further stirred for 1 hour. The reaction mixture was analyzed by high performance liquid chromatography. As a result, THP-1H-indazole boronic acid pinacol ester and THP-2H-indazole boronic acid pinacol ester were contained in a total amount of 0.23 g (0.71 mmol, yield: 83%).

Production of Other Compounds

Example 14

4,4,5,5-tetramethyl-1,3,2-dioxaborolan-2-yl)benzene

Under a nitrogen atmosphere, a reaction vessel of 20 ml in volume was charged with bis(pinacolate)diboron (1.35 g (5.3 mmol)), degassed methanol (7.2 g) and triethylamine (1.08 g (10.7 mmol)) and stirred at room temperature. The reaction vessel was charged with bis(1,5-cyclooctadiene)nickel (39 mg (0.14 mmol)), triphenylphosphine (75 mg (0.28 mmol)), and chlorobenzene (0.40 g (3.6 mmol)) and stirred at 30° C. for 21 hours. The reaction solution was analyzed by gas chromatography. As a result, (4,4,5,5-tetramethyl-1,3,2-dioxaborolan-2-yl)benzene was contained in an amount of 0.50 g (2.5 mmol, yield: 69%).

Examples 15 to 17

A reaction was performed in the same manner as in Example 14 except that the bases listed in Table 4 were used in place of triethylamine and the charge amounts thereof were changed to those listed in Table 4. The results are shown in Table 4.

TABLE 4

|  | Example 15 | Example 16 | Example 17 |
|---|---|---|---|
| Base | Diisopropylethylamine | N-methylmorpholine | DBU* |
| Weight | 1.38 g | 1.08 g | 1.62 g |
| Mole | 10.7 mmol | 10.7 mmol | 10.7 mmol |
| Yield | 78% | 67% | 61% |

*"DBU" represents 1,8-diazabicyclo[5.4.0]-7-undecene

Example 18

(4,4,5,5-tetramethyl-1,3,2-dioxaborolan-2-yl)benzene

Under a nitrogen atmosphere, a reaction vessel of 20 ml in volume was charged with bis(pinacolate)diboron (1.35 g (5.3 mmol)), degassed methanol (7.2 g) and diisopropylethylamine (1.38 g (10.7 mmol)) and stirred at room temperature. The reaction vessel was charged with bis(1,5-cyclooctadiene)nickel (39 mg (0.14 mmol)), triphenylphosphine (75 mg (0.28 mmol)), and chlorobenzene (0.44 g (3.9 mmol)) and stirred at 30° C. for 21 hours and thereafter stirred at 50° C., 4 hours. The reaction solution was analyzed by gas chromatography. As a result, (4,4,5,5-tetramethyl-1,3,2-dioxaborolan-2-yl)benzene was contained in an amount of 0.79 g (3.9 mmol, yield: 99%).

Example 19

(4,4,5,5-tetramethyl-1,3,2-dioxaborolan-2-yl)benzene

Under a nitrogen atmosphere, a reaction vessel of 20 ml in volume was charged with bis(pinacolate)diboron (1.35 g (5.3 mmol)), degassed methanol (7.2 g) and diisopropylethylamine (1.38 g, (10.7 mmol)) and stirred at room temperature. The reaction vessel was charged with nickel nitrate hexahydrate (41 mg (0.14 mmol)), triphenylphosphine (75 mg (0.28 mmol)) and chlorobenzene (0.40 g (3.6 mmol)) and stirred at 30° C. for 21 hours, and thereafter stirred at 50° C., 4 hours. The reaction solution was analyzed by gas chromatography. As a result, (4,4,5,5-tetramethyl-1,3,2-dioxaborolan-2-yl)benzene was contained in an amount of 0.65 g (3.2 mmol, yield: 90%).

Example 20

A reaction was performed in the same manner as in Example 19 except that the catalyst listed in Table 5 was used in place of nickel nitrate hexahydrate and the use amount thereof was changed to that listed in Table 5. The results are shown in Table 5.

TABLE 5

|  | Example 20 |
|---|---|
| Catalyst | Nickel(II) chloride |
| Weight | 19 mg |
| Mole | 0.14 mmol |
| Yield | 74% |

Example 21

(4,4,5,5-tetramethyl-1,3,2-dioxaborolan-2-yl)benzene

Under a nitrogen atmosphere, a reaction vessel of 20 ml in volume was charged with bis(pinacolate)diboron (0.97 g (3.8 mmol)), degassed methanol (7.2 g) and diisopropylethylamine (0.99 g (7.6 mmol)) and stirred at room temperature. The reaction vessel was charged with bis(1,5-cyclooctadiene)nickel (28 mg (0.10 mmol)), triphenylphosphine (53 mg (0.20 mmol)), and bromobenzene (0.40 g (2.5 mmol)) and stirred at 30° C. for 21 hours. The reaction solution was analyzed by gas chromatography. As a result, (4,4,5,5-tetramethyl-1,3,2-dioxaborolan-2-yl)benzene was contained in an amount of 0.40 g (2.0 mmol, yield: 77%).

Example 22

(4,4,5,5-tetramethyl-1,3,2-dioxaborolan-2-yl)benzene

Under a nitrogen atmosphere, a reaction vessel of 20 ml in volume was charged with bis(pinacolate)diboron (0.75 g (2.9 mmol)), degassed methanol (7.2 g) and diisopropylethylamine (0.76 g (5.9 mmol)) and stirred at room temperature. The reaction vessel was charged with bis(1,5-cyclooctadiene)nickel (22 mg (0.1 mmol)), triphenylphosphine (41 mg (0.2 mmol)), and iodobenzene (0.44 g (2.2 mmol)) and stirred at 30° C. for 21 hours. The reaction solution was analyzed by gas chromatography. As a result, (4,4,5,5-tetramethyl-1,3,2-dioxaborolan-2-yl)benzene was contained in an amount of 0.41 g (2.0 mmol, yield: 93%).

Example 23

4-(4,4,5,5-tetramethyl-1,3,2-dioxaborolan-2-yl)toluene

Under a nitrogen atmosphere, a reaction vessel of 20 ml in volume was charged with bis(pinacolate)diboron (1.20 g (4.7 mmol)), degassed methanol (7.2 g) and diisopropylethylamine (1.23 g (9.5 mmol)) and stirred at room temperature. The reaction vessel was charged with bis(1,5-cyclooctadiene)nickel (35 mg (0.13 mmol)), triphenylphosphine (66 mg (0.25 mmol)), and 4-chlorotoluene (0.40 g (3.2 mmol)) and stirred at 30° C. for 21 hours, and thereafter at 50° C. for 3 hours. The reaction solution was analyzed by gas chromatography. As a result, 4-(4,4,5,5-tetramethyl-1,3,2-dioxaborolan-2-yl)toluene was contained in an amount of 0.41 g (1.9 mmol, yield: 60%).

Example 24

4-(4,4,5,5-tetramethyl-1,3,2-dioxaborolan-2-yl)anisole

Under a nitrogen atmosphere, a reaction vessel of 20 ml in volume was charged with bis(pinacolate)diboron (1.07 g (4.2 mmol)), degassed methanol (7.2 g) and diisopropylethylamine (1.09 g (8.4 mmol)) and stirred at room temperature. The reaction vessel was charged with bis(1,5-cyclooctadiene)nickel (31 mg (0.11 mmol)), triphenylphosphine (59 mg (0.22 mmol)), and 4-chloroanisole (0.40 g (2.8 mmol)), and stirred at 30° C. for 21 hours and thereafter, stirred at 50° C. for 3 hours. The reaction solution was analyzed by gas chromatography. As a result, 4-(4,4,5,5-tetramethyl-1,3,2-dioxaborolan-2-yl)anisole was contained in an amount of 0.58 g (2.7 mmol, yield: 97%).

Example 25

4-(4,4,5,5-tetramethyl-1,3,2-dioxaborolan-2-yl)acetophenone

Under a nitrogen atmosphere, a reaction vessel of 20 ml in volume was charged with bis(pinacolate)diboron (0.99 g (3.9 mmol)), degassed methanol (7.2 g) and diisopropylethylamine (1.00 g (7.8 mmol)) and stirred at room temperature. The reaction vessel was charged with bis(1,5-cyclooctadiene)nickel (28 mg (0.10 mmol)), triphenylphosphine (54 mg (0.21 mmol)), and 4'-chloroacetophenone (0.40 g (2.6 mmol)) and stirred at 30° C. for 21 hours, and thereafter stirred at 50° C. for 3 hours. The reaction solution was analyzed by gas chromatography. As a result, 4-(4,4,5,5-tetramethyl-1,3,2-dioxaborolan-2-yl)acetophenone was contained in an amount of 0.58 g (2.4 mmol, yield: 91%).

Example 26

4-(4,4,5,5-tetramethyl-1,3,2-dioxaborolan-2-yl)benzonitrile

Under a nitrogen atmosphere, a reaction vessel of 20 ml in volume was charged with bis(pinacolate)diboron (1.11 g (4.4 mmol)), degassed methanol (7.2 g) and diisopropylethylamine (1.13 g (8.7 mmol)) and stirred at room temperature. The reaction vessel was charged with bis(1,5-cyclooctadiene)nickel (32 mg (0.12 mmol)), triphenylphosphine (61 mg (0.23 mmol)), and 4-chlorobenzonitrile (0.40 g (2.9 mmol)) and stirred at 30° C. for 21 hours, and thereafter stirred at 50° C. for 3 hours. The reaction solution was analyzed by gas chromatography. As a result, 4-(4,4,5,5-tetramethyl-1,3,2-dioxaborolan-2-yl)benzonitrile was contained in an amount of 0.58 g (2.6 mmol, yield: 88%).

Example 27

3-(4,4,5,5-tetramethyl-1,2-dioxaborolan-2-yl)pyridine

Under a nitrogen atmosphere, a reaction vessel of 20 ml in volume was charged with bis(pinacolate)diboron (1.34 g (5.3 mmol)), degassed methanol (7.2 g) and diisopropylethylamine (1.36 g (10.6 mmol)) and stirred at room temperature. The reaction vessel was charged with bis(1,5-cyclooctadiene)nickel (39 mg (0.14 mmol)), triphenylphosphine (74 mg (0.28 mmol)), and 3-chloropyridine (0.40 g (3.52 mmol)) and stirred at 30° C. for 21 hours, and thereafter stirred at 50° C. for 3 hours. The reaction solution was analyzed by gas chromatography. As a result, 3-(4,4,5,5-tetramethyl-1,3,2-dioxaborolan-2-yl)pyridine was contained in an amount of 0.29 g (1.42 mmol, yield: 41%).

Example 28

4-(4,4,5,5-tetramethyl-1,3,2-dioxaborolan-2-yl)indole

Under a nitrogen atmosphere, a reaction vessel of 20 ml in volume was charged with bis(pinacolate)diboron (0.50 g (2.0 mmol)), degassed methanol (7.2 g) and diisopropylethylamine (0.51 g (4.0 mmol)) and stirred at room temperature. The reaction vessel was charged with bis(1,5-cyclooctadiene)nickel (15 mg (0.05 mmol)), triphenylphosphine (28 mg (0.11 mmol)), and 4-chloroindole (0.20 g (1.32 mmol)) and stirred at 30° C. for 21 hours, and thereafter stirred at 50° C. for 3 hours. The reaction solution was analyzed by gas chromatography. As a result, 4-(4,4,5,5-tetramethyl-1,3,2-dioxaborolan-2-yl)indole was contained in an amount of 0.26 g (1.05 mmol, yield: 80%).

Example 29

2-amino-6-(4,4,5,5-tetramethyl-1,3,2-dioxaborolan-2-yl)toluene

Under a nitrogen atmosphere, a reaction vessel of 20 ml in volume was charged with bis(pinacolate)diboron (1.08 g (4.2 mmol)), degassed methanol (7.2 g) and diisopropylethylamine (1.10 g (8.5 mmol)) and stirred at room temperature. The reaction vessel was charged with bis(1,5-cyclooctadiene)nickel (31 mg (0.11 mmol)), triphenylphosphine (59 mg (0.23 mmol)), and 2-amino-6-chlorotoluene (0.40 g (2.82 mmol)) and stirred at 30° C. for 21 hours, and thereafter stirred at 50° C. for 3 hours. The reaction solution was analyzed by gas chromatography. As a result, 2-amino-6-(4,4,5,5-tetramethyl-1,3,2-dioxaborolan-2-yl)toluene was contained in an amount of 0.26 g (1.11 mmol, yield: 40%).

Example 30

Mixture of THP-1H-indazole boronic acid pinacol ester and THP-2H-indazole boronic acid pinacol ester Under a nitrogen atmosphere, a reaction vessel was charged with bis(pinacolate)diboron (11.07 kg (43.6 mol)), methanol (23.8 kg), triethylamine (8.83 kg (87.2 mol)) and a mixture (15.49 kg (chloro-THP-1H-indazole: 3.2 wt %, chloro-THP-2H-indazole: 48.1 wt %, total: 33.54 mol)) of chloro-THP-1H-indazole and chloro-THP-2H-indazole manufactured in accordance with Manufacturing Example 2. After the interior temperature was reduced to 6° C., the reaction vessel was vacuumed and then purged with nitrogen. Then, the reaction vessel was charged with nickel nitrate hexahydrate (0.39 kg (1.3 mol)) and triphenylphosphine (0.70 kg (2.7 mol)). The resultant reaction mixture was increased in temperature to an interior temperature of 20° C. and stirred for 7 hours. The reaction mixture was analyzed by high performance liquid chromatography. As a result, the reaction mixture contained THP-1H-indazole boronic acid pinacol ester and THP-2H-indazole boronic acid pinacol ester in a total amount of 8.54 kg (26.02 mol, yield: 77.6%).

To the reaction mixture, tert-butyl methyl ether (87.3 kg) and 5 wt % hydrochloric acid (34.5 kg) were added and the pH of the mixture was adjusted to 7.5 and then liquid separation was performed. To the obtained water phase, tert-butyl methyl ether (71.5 kg) was added to perform re-extraction. The organic phases individually obtained were combined, water phase was separated and the organic phase was concentrated under reduced pressure. To the resultant concentrate, toluene (31.8 kg) was added and concentrated under reduced pressure. To the concentrate, toluene (23.8 kg) and a 20 wt % aqueous methanol solution (29.8 kg) were added, mixed and separated. Furthermore, to the resultant organic phase, a 20 wt % aqueous methanol solution (29.8 kg) was added, mixed and separated. This operation was repeated twice. To the obtained organic phase, activated carbon (0.4 kg) was added, stirred at room temperature for one hour and filtrated. The filtrate was concentrated under reduced pressure to obtain a concentrate of 14.7 kg. The obtained concentrate was analyzed by gas chromatography and high performance liquid chromatography. As a result, the concentrate contained THP-1H-indazole boronic acid pinacol ester and THP-2H-indazole boronic acid pinacol ester in a content of 56.4 wt % (THP-1H-indazole boronic acid pinacol ester=3.1 wt %, THP-2H-indazole boronic acid pinacol ester=53.3 wt %, toluene=20.4 wt %). Furthermore, ICP emission analysis was performed herein. As a result, the concentrate contained 0.74 g of nickel (the residual ratio of nickel was 0.94 wt % based on the charge amount of nickel). To the concentrate, toluene (2.0 kg) and heptane (11.6 kg) were added and heated to 48° C. To the mixture, a seed crystal (1 g) containing a mixture of THP-1H-indazole boronic acid pinacol ester and THP-2H-indazole boronic acid pinacol ester was added. As a result, crystals precipitated. Thereafter, the mixture was cooled to 0° C. for 9 hours and 50 minutes, again increased in temperature to 20° C., then cooled to 2° C., and filtrated. The crystals obtained were washed with a mixed solution (0° C.) of heptane (2.2 kg) and toluene (1.0 kg) and filtrated. The remaining crystals were dried under reduced pressure to obtain crystals (6.29 kg). The crystals obtained were analyzed by the high performance liquid chromatography internal standard method. As a result, the crystals contained THP-1H-indazole boronic acid pinacol ester (0.4 wt %) and THP-2H-indazole boronic acid pinacol ester (88.0 wt %) in a total amount of 5.56 kg (16.9 mol, yield: 50.5%). Furthermore, ICP emission analysis was performed. As a result, the content of nickel in the crystals was 42 ppm (nickel fineness: 0.26 g (the residual ratio of nickel was 0.34 wt % based on the charge amount of nickel)). Methanol was added to dissolve the crystals remaining in the reaction vessel, and the obtained solution was analyzed by the high performance liquid chromatography internal standard method. As a result, the solution contained THP-1H-indazole boronic acid pinacol ester and THP-2H-indazole boronic acid pinacol ester in a total amount of 0.50 kg (1.53 mol, yield: 4.6%).

INDUSTRIAL APPLICABILITY

The boronic acid ester compounds obtained by the manufacturing method of the present invention, in particular, a boronic acid ester compound having an indazole skeleton is useful as e.g. an intermediate for synthesizing medical/agricultural drugs (see, for example, WO 2007/127183, WO 2006/046031, WO 2006/046040, WO 2006/046035, WO 2007/129161, WO 2007/132171, WO 2007/127175, WO 2008/073785, WO 2008/070740).

The invention claimed is:
1. A method for preparing a boronic acid ester compound represented by formula (3):

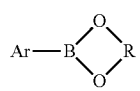

(3)

wherein Ar represents an optionally substituted aromatic hydrocarbon group, or an optionally substituted aromatic heterocyclic group;
R represents a an optionally substituted alkylene group, or an optionally substituted arylene group;
characterized by reacting a compound represented by formula (1):

(1)

wherein Ar is as defined above,

X represents a halogen atom, an optionally substituted alkylsulfonyloxy group, or an optionally substituted arylsulfonyloxy group;
with a compound represented by formula (2):

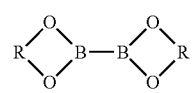

(2)

wherein R is as defined above;
in the presence of a nitrogen-containing organic base, a nickel catalyst, a phosphine compound and a solvent.
2. The method for preparing the boronic acid ester compound according to claim 1, wherein Ar is an optionally substituted aromatic hydrocarbon group, an optionally substituted nitrogen-containing aromatic heterocyclic group, an optionally substituted sulfur-containing aromatic heterocyclic group, or an optionally substituted oxygen-containing aromatic heterocyclic group.
3. The method for preparing the boronic acid ester compound according to claim 1, wherein Ar is an optionally substituted aromatic hydrocarbon group, or an optionally substituted nitrogen-containing aromatic heterocyclic group.
4. The method for preparing the boronic acid ester compound according to claim 1, wherein Ar is an optionally substituted phenyl group, an optionally substituted pyridyl group, an optionally substituted indolyl group, or an optionally substituted indazolyl group.
5. The method for preparing the boronic acid ester compound according to claim 1, wherein the nickel catalyst is a 0-valent or divalent nickel complex.
6. The method for preparing the boronic acid ester compound according to claim 1, wherein the nickel catalyst is at least one nickel complex selected from the group consisting of a nickel(0)-alkene complex, a nickel(0)-phosphine complex, a nickel(0)-phosphite complex, an inorganic acid salt of nickel(II), an organic acid salt of nickel(II), a nickel(II) halide, and a nickel(II) halide-phosphine complex.
7. The method for preparing the boronic acid ester compound according to claim 1, wherein the nickel catalyst is bis(1,5-cyclooctadiene)nickel(0), nickel(II) nitrate or nickel (II) chloride.
8. The method for preparing the boronic acid ester compound according to claim 1, wherein the nitrogen-containing organic base is a tertiary amine compound or a cyclic amidine compound.
9. The method for preparing the boronic acid ester compound according to claim 1, wherein the nitrogen-containing organic base is a trialkylamine compound, a cyclic tertiary amine compound or a cyclic amidine compound.
10. The method for preparing the boronic acid ester compound according to claim 1, wherein the nitrogen-containing organic base is triethylamine, diisopropylethylamine, N-methylmorpholine or 1,8-diazabicyclo[5.4.0]-7-undecene.
11. The method for preparing the boronic acid ester compound according to claim 1, wherein the phosphine compound is a triarylphosphine.
12. The method for preparing the boronic acid ester compound according to claim 1, wherein the phosphine compound is triphenylphosphine.
13. The method for preparing the boronic acid ester compound according to claim 1, wherein the solvent is an alcohol solvent, or a mixed solvent of an alcohol solvent and at least one solvent selected from the group consisting of a hydrocarbon solvent, an ether solvent, an ester solvent, a ketone solvent, an amide solvent, a nitrile solvent, a sulfoxide solvent and a halogenated hydrocarbon solvent.

14. The method for preparing the boronic acid ester compound according to claim 1, wherein the solvent is an alcohol solvent, or a mixed solvent of an alcohol solvent and at least one solvent selected from the group consisting of a hydrocarbon solvent, an ether solvent, and an ester solvent.

15. The method for preparing the boronic acid ester compound according to claim 13, wherein the alcohol solvent is methanol or ethanol.

16. The method for preparing the boronic acid ester compound according to claim 13, wherein the alcohol solvent is methanol.

17. The method for preparing the boronic acid ester compound according to claim 1, wherein the compound represented by formula (2) is bis(pinacolate)diboron.

18. The method for preparing the boronic acid ester compound according to claim 1, wherein X is a chlorine atom, a bromine atom, an iodine atom, a methanesulfonyloxy group, a trifluoromethanesulfonyloxy group, a toluenesulfonyloxy group or a benzenesulfonyloxy group.

19. The method for preparing the boronic acid ester compound according to claim 1, wherein X is a chlorine atom, a bromine atom, or an iodine atom.

20. The method for preparing the boronic acid ester compound according to claim 1, wherein Ar is an aromatic heterocyclic group selected from the group consisting of the following:

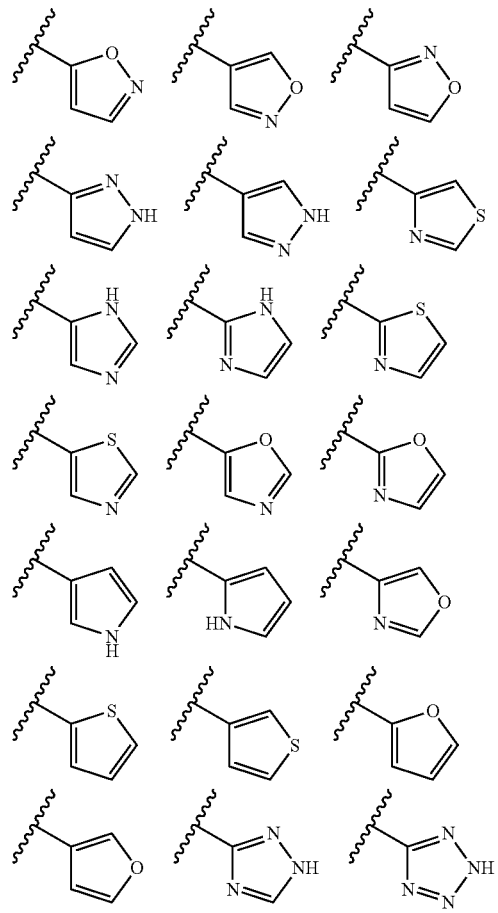

-continued

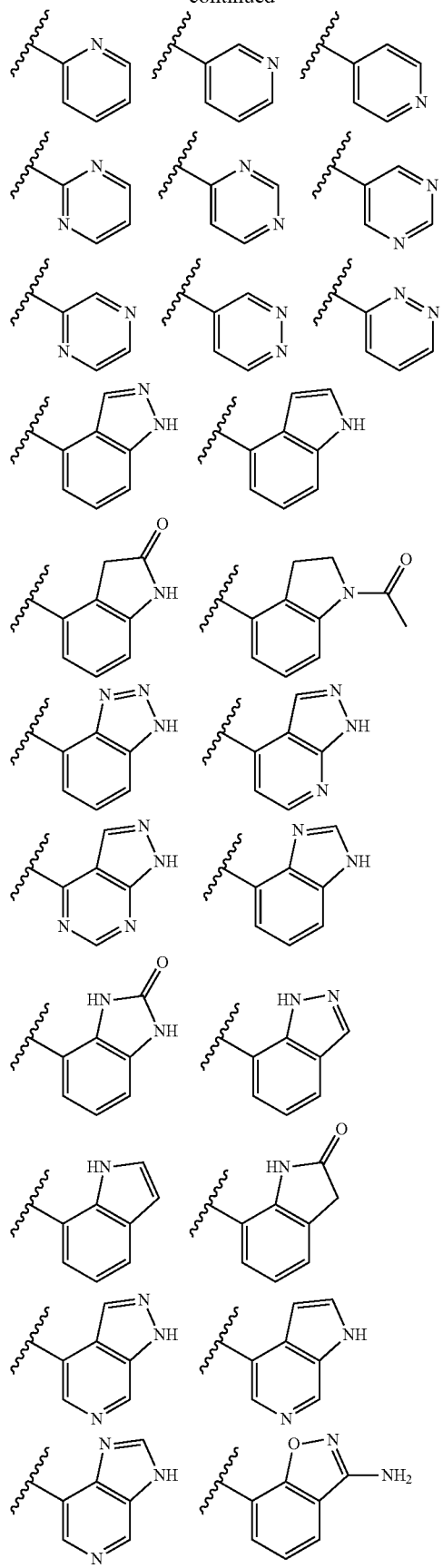

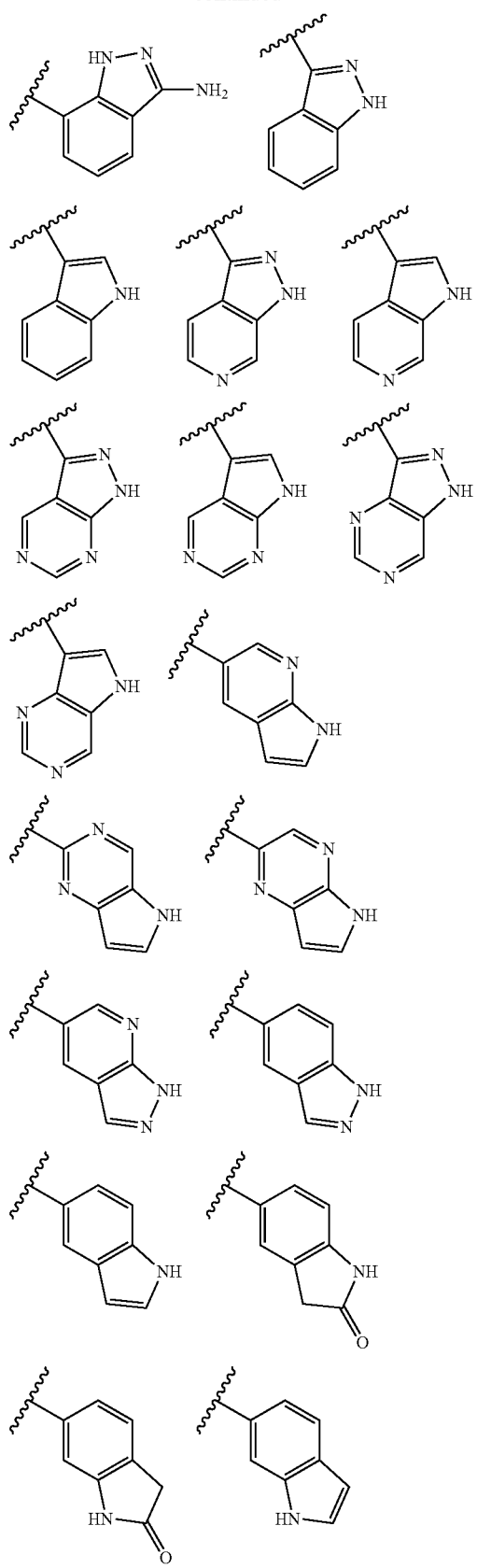
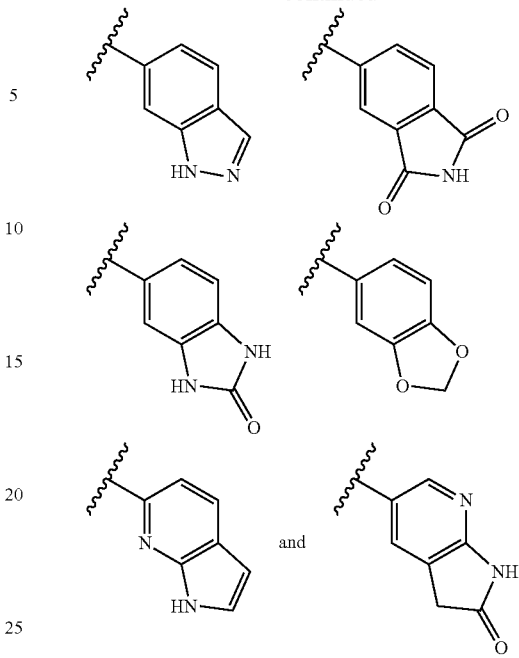

where the wavy lines indicate the bonding position of Ar, and the above groups may be substituted.

21. The method for preparing the boronic acid ester compound according to claim 20, wherein the aromatic heterocyclic group is substituted with one or more groups selected from the group consisting of a fluorine atom, a chlorine atom, a bromine atom, an iodine atom, a methyl group, a cyano group, a trifluoromethyl group, a hydroxymethyl group, a carboxy group, a carbamoyl group, an N,N-dimethylcarbamoyl group, a nitro group, an amino group, an N-methylamino group, N-acetylamino group, a hydroxy group, a methoxy group, a sulfanyl group, a methylsulfonyl group, and a group represented by the formula —NHC(=O)NHCH$_3$.

22. The method for preparing the boronic acid ester compound according to claim 1, wherein the compound represented by formula (1) is the compound represented by the following formula:

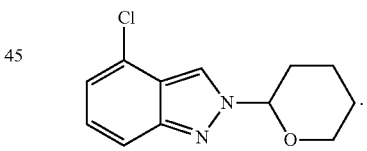

23. The method for preparing the boronic acid ester compound according to claim 1, wherein the compound represented by formula (3) is the compound represented by the following formula:

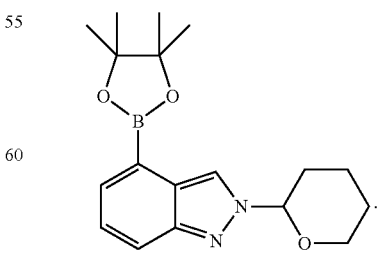

* * * * *